United States Patent
Iori

(10) Patent No.: US 7,384,927 B2
(45) Date of Patent: Jun. 10, 2008

(54) ALKYLATED PORPHYRINS AS PESTICIDES ACTING BOTH IN THE PRESENCE AND ABSENCE OF LIGHT

(76) Inventor: Giulio Iori, Via Cavalieri Bonaventura, 18 - 35143 - Padova (IT)

( * ) Notice: Subject to any disclaimer, the term of this patent is extended or adjusted under 35 U.S.C. 154(b) by 0 days.

(21) Appl. No.: 10/994,252

(22) Filed: Nov. 23, 2004

(65) Prior Publication Data
US 2005/0197324 A1 Sep. 8, 2005

Related U.S. Application Data

(63) Continuation-in-part of application No. 10/510,832, filed as application No. PCT/IB2004/000725 on Mar. 11, 2004, now abandoned.

(30) Foreign Application Priority Data

Mar. 12, 2003 (EP) .................................. 03005340

(51) Int. Cl.
*A01N 55/02* (2006.01)
(52) U.S. Cl. ...................................................... 514/185
(58) Field of Classification Search ................. 514/185
See application file for complete search history.

(56) References Cited

U.S. PATENT DOCUMENTS 5,431,883 A * 7/1995 Barraud ................... 422/82.01
6,410,567 B1 * 6/2002 Jori .............................. 514/333
6,573,258 B2 * 6/2003 Bommer et al. ............. 514/185
2003/0153546 A1 * 8/2003 Schaffer et al. ............. 514/185

FOREIGN PATENT DOCUMENTS

WO  WO 97/29636 A1   8/1997
WO  WO 97/29637 A1   8/1997

OTHER PUBLICATIONS

O'Driscoll et al (Cationic amphiphilic porphyrin on saline subphases, J. of Porphyrin and Phthalocyanines, 2002, 6(11-12), 806-811).*
Hanack et al (Phthalocyaninatoiron complexes with tridentate ligands, Synthetic Metals, 1999, 100, (1), 123-130). ABS.*
Soncin et al (Approaches to selectivity in the Zn(II)-phthalocyanine-photosensitized inactivation of wild-type and antibiotic-resistant *Staphylococcus aureus*, Photochemical & Photobiological Sciences, 2002, 1 (10), 815-9). ABS.*
Amor et al., Photochemistry and PHotobiology, vol. 68, No. 3, pp. 314-318 (1998).
Amor, Photochemistry and Photobiology, vol. 71, No. 2, pp. 124-128 (2000) (Abstract Only)—XP-002246062.

* cited by examiner

*Primary Examiner*—Alton Pryor
(74) *Attorney, Agent, or Firm*—Birch, Stewart, Kolasch & Birch, LLP

(57) ABSTRACT

An insecticidal composition comprising at least one compound of the tetrapyrrole series having at least one hydrocarbon chain at least 12 carbon atoms long as a peripheral substituent, wherein the compound of the tetrapyrrole series is selected from porphyrins, chlorins, phthalocyanines or naphthalocyanines.

10 Claims, 3 Drawing Sheets

Figure 1:
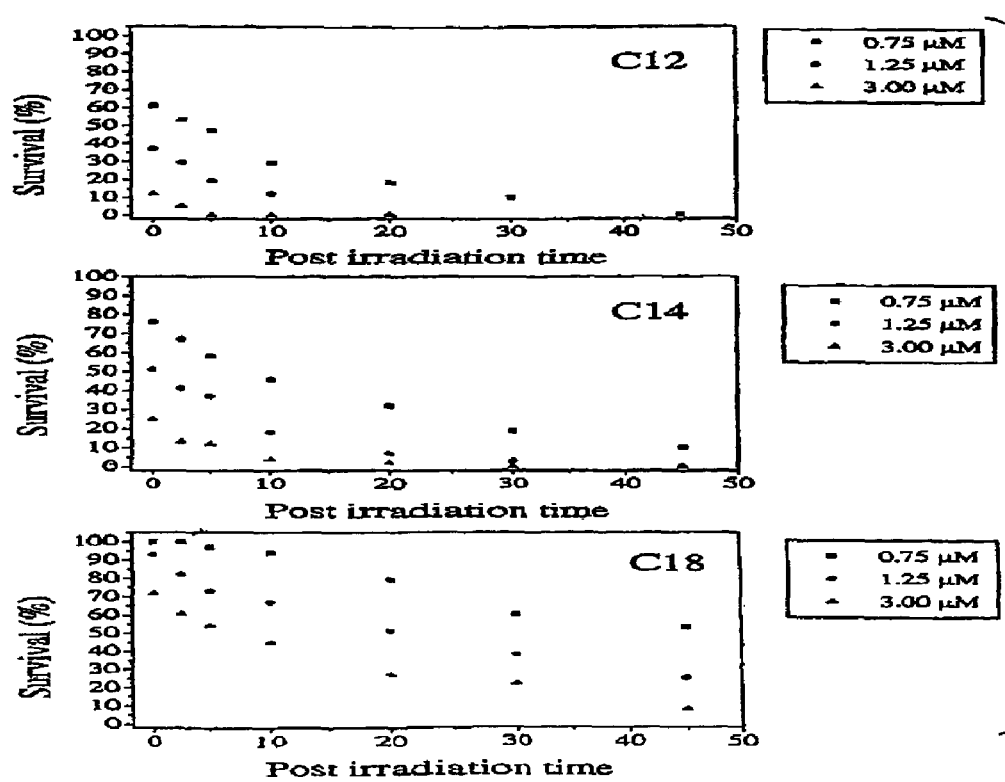

ALKYLATED PORPHYRINS AS PESTICIDES ACTING BOTH IN THE PRESENCE AND ABSENCE OF LIGHT

This application is a Continuation-In-Part of U.S. application Ser. No. 10/510,832, filed on Oct. 12, 2004 now abandoned, which is the national phase under 35 U.S.C. § 371 of PCT International Application No. PCT/IB04/000725 which has an International filing date of Mar. 11, 2004, for which priority is claimed under 35 U.S.C. § 120. This application also claims priority to European Application No. 03005340.9, filed in Europe on Mar. 12, 2003 under 35 U.S.C. § 119(e).

The use of photochemical processes as a tool to control the population of noxious insects, which are known to cause extensive damage to crop plants and to act as carriers of a wide variety of diseases to humans and animals, has given very positive results in both laboratory and field studies. An historical development and the state-of-the-art of this technology have been described, for example, in Heitz J. R., *Photochem. Photobiol.* 65:TPM-D1, 1997; Ben Amor T., Jori G., *Insect Biochem. Mol. Biol.* 30:915, 2000. Most investigations have been performed by using photoactivatable polycyclic aromatic compounds, that absorb near-UV (360-400 nm) and/or visible (400-800 nm) light wavelengths, such as thiophenes, quinones and xanthene derivatives. Such photosensitizing compounds have several advantageous features as compared with many out of the presently used chemical toxicants for insects, which are characterized by several hazards for consumers and the environment (see Lemke L. A., Koehler P. G., Patterson R. S., Feger M. B., Eickhoff T., in *Light Activated Pesticides*, Edited by Heitz J. R. and Dowrum K. R., ACS, Washington, 1997, 99. 156-167). Recently, porphyrin-type photosensitizers have been proposed as novel photoinsecticidal agents (Rebeiz C. A., Reddy K. N., Nandihall U. B., Velu J., *Photochem. Photobiol.* 52:1099, 1990; Ben Amor T., Tronchin M., Bortolotto L., Verdiglione L., Jori G., *Photochem. Photobiol.* 67:206, 1998). In actual fact, porphyrins are endowed with favourable properties to act as phototoxins against insects. Such properties include:

(a) The ability to absorb essentially all the wavelengths of the solar spectrum in the UV and visible range: thus, they can be efficiently photoactivated by both blue light (which is the most intense component of the sun emission around midday) and red light (which is the dominant component of sunlight at dawn and sunset); this makes it possible to use porphyrin dosages which are lower than those typical of other photosensitizers.

(b) Long-lived photogenerated electronically excited states guarantee that porphyrins can diffuse over relatively large distances before undergoing deactivation, thereby increasing the probability of their interaction with suitable targets which are critical for cell function and survival.

(c) Lack of mutagenic potential associated with porphyrin-promoted photoprocesses, which also minimizes the risk of selecting photoresistant insect species.

(d) Essentially negligible cytotoxicity of porphyrins, which can be coupled with their ready water-solubility and gradual photobleaching under the action of visible light. All these properties warrant that even a widespread utilization of porphyrins has no appreciable impact on the environment.

The photoinsecticidal properties of selected porphyrins and some porphyrin derivatives (such as phthalocyanines) are described and discussed in patent application WO97/29637.

An object of the present invention is to provide porphyrins that are highly toxic against a variety of noxious insects even in the absence of light.

Another object of the present invention is to provide porphyrins capable of inducing extensive photoinduced mortality in insects at doses which are at least ten-fold smaller than those causing an equivalent degree of insect death in the presence of conventionally used porphyrins.

According to the present invention there is provided an insecticidal composition characterized in that it comprises at least one compound of the tetrapyrrole series having at least one hydrocarbon chain of at least 12 carbon atoms as a peripheral substituent.

Advantagesously, the said compound comprises at least one meso-substituted tetracationic porphyrin of the general chemical structure

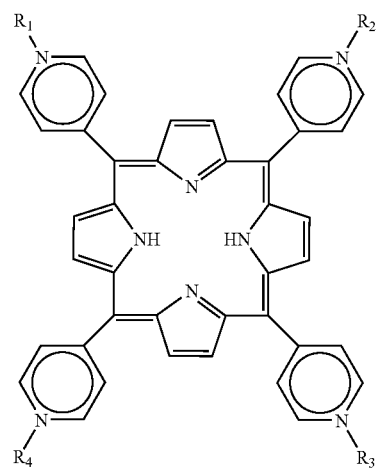

wherein at least one peripheral substituent indicated as $R_1$ $R_2$, $R_3$ or $R_4$ comprises a saturated hydrocarbon chain containing at least 12 carbon atoms.

Advantageously, $R_1=R_2=R_{3=R4}=$an alkyl chain of variable length ranging from one to twenty carbon atoms.

Typically, $R_1=R_2=R_3=CH_3$ $R_4=C_{12} H_{23}$ $(C_{12})$
$R_1=R_2=R_3=CH_3$ $R_4=C_{14} H_{27}$ $(C_{14})$
$R_1=R_2=R_3=CH_3$ $R_4=C_{18} H_{35}$ $(C_{18})$ It was found that the class of meso-substituted tetracationic porphyrins according to the present invention besides displaying a high toxicity against a variety of noxious insects even in the absence of light when administered at submicromolar doses, induces an extensive photoinduced mortality of the insects at doses which are at least ten-fold smaller than those causing an equivalent degree of insect death in the presence of conventionally used porphyrins.

Typical, but by no means exclusive, of especially active porphyrin composition according to the invention are those including a porphyrine selected in the group comprising: meso-tri(N-methyl-pyridyl), mono(N-tetradecyl-pyridyl) porphine and its mono-C12, mono-C18 analogues, as well as meso-tetra(N-tetradecyl-pyridyl)porphine.

In the following description, the expression "pest control" refers to the control of organisms which are suitable for causing damage to man, his useful animals, crop plants and, in general, his economy. The term "pesticides" indicates compositions which are effective for controlling plant pests (crop or plant protection compositions) as well as for controlling other kinds of pests or troublesome organisms. Plant pest group includes insects and/or their larvae. A first group includes, in particular, flies, fruit flies, bugs, mosquitoes or fleas which are able to transmit diseases to humans and animals, and pests for stored products, such as cockroaches, beetles or moths.

The term "porphyrins" refers to meso-substituted tetra-N-alkylated porphyrins which produce a lethal effect on pests when administered at micromolar doses in association with a suitable bait and whose insecticidal action is further increased by irradiation with light wavelengths in the spectral range from about 350 to 800 nm.

More particularly, the present invention concerns the association of a porphyrin with a biological or chemical attractant which can be selected from a variety of available substances, e.g., to name but a few, buminal, grandisol, bombykol, frontalin, or pheromones, depending on the particular pest to be controlled. The attractants make the pest approach the food source containing the photosensitizer, and increase the voracity of the pests so that larger amounts of porphyrins are ingested. In the control of pests, the pesticide can be broadcast in the environment in an appropriate manner. For example, the pesticide can be laid out as food in the crop plant area to be treated, can be offered to the pests in traps positioned in carefully selected sites in the field, or can be sprayed in the form of an aqueous solution.

Following intake of the pesticide into the respective pest organism, the porphyrin becomes bound to membranous systems of cells in various tissues, including the midgut wall and neuromuscular sheath (see Ben Amor T., Bortolotto L., Jori G., *Photochem. Photobiol.* 68:314, 1998). The long hydrocarbon arm in the porphyrin molecule is likely to interfere with the organized structure of the lipid domains in the cell membranes, thereby altering the native architecture and impairing several metabolic processes. The overall result can be summarized as inhibition of insect feeding, as well as of its ability to fly or move. These effects are enhanced by illuminating the insect with light wavelengths absorbed by the ingested porphyrin, bearing in mind that visible light has a penetration power of 0.5-2 cm into most biological tissues depending on the wavelength and the degree of tissue pigmentation (Svaasand L. O., Martinelli E., Gomer C. J., Profio A. E., *Proc. SPIE* 1203:2, 1990). The porphyrin can be photoactivated even if it is localized in internal organs. The photoexcited porphyrins transfer electronic energy to nearby substrates, especially oxygen with generation of hyperreactive oxygen species (e. g., singlet oxygen, hydroxyl radicals) leading to oxidative irreversible modification of membranes and other subcellular organelles.

Table 1 illustrates the experimental protocol used for demonstrating the pesticidal action of alkylated porphyrins.

TABLE 1

Experimental protocol used for testing the (photo)insecticidal activity of alkylated porphyrins at a laboratoiy level.

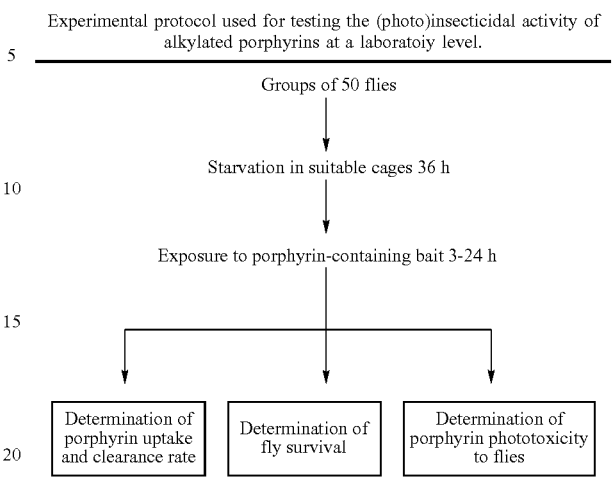

Porphyrins:
a) meso[tri(N-methyl-pyridyl), mono(N-dodecyl-pyridyl)] porphine (abbr.: C12)
b) meso[tri(N-methyl-pyridyl), mono(N-tetradecyl-pyridyl)]porphine (abbr.: C14)
c) meso[tri(N-methyl-pyridyl), mono(N-octadecyl-pyridyl)] porphine (abbr.: C18)

Bait:

Aqueous solution containing 10% sucrose and 1% autolysed yeast

Flies:
a) *Ceratitis capitata* (fruit fly) age: 1 week; weight: 5-6 mg
b) *Bactrocera oleae* (olive fly) age: 10 days; weight: 4-4.5 mg
c) *Stomoxis calcitrans* (stable fly) age: 10 days; weight: 12 mg Irradiation:
a) High pressure halogen lamp, equipped with infrared and UV filters, emission 360-850 nm, operated at intensities in the 760-2,000 $\mu E\ s^{-1}m^{-2}$ range
b) Sunlight, mid June at Padua latitude, average intensity of 1,500 $\mu E\ s^{-1}m^{-2}$ with minimum and maximum values of 950 and, respectively, 1,380 $\mu E\ s^{-1}m^{-2}$ Tables 2 and 3 show the amount of porphyrin accumulation by typical flies as a function of porphyrin concentration and, respectively, the time of exposure of the insect to the porphyrin/bait formulation.

TABLE 2

Uptake of alkylated porphyrins by flies as a function of porphyrin concentration in the bait after feeding for 24 h.

| Porphyrin concentration | Recoveries (nmoles of porphyrin per fly) | | |
| --- | --- | --- | --- |
| (µmoles) | *C. capitata* | *B. oleae* | *S. calcitrans* |
| C12 | | | |
| 0.00 | n.d. | n.d | n.d |
| 0.75 | 2.9 | 2.7 | 2.5 |
| 1.25 | 4.1 | 3.2 | 3.7 |
| 2.10 | 7.3 | 6.5 | 6.0 |

TABLE 2-continued

Uptake of alkylated porphyrins by flies as a function of porphyrin concentration in the bait after feeding for 24 h.

| Porphyrin concentration | Recoveries (nmoles of porphyrin per fly) | | |
|---|---|---|---|
| (µmoles) | C. capitata | B. oleae | S. calcitrans |
| 3.50 | 9.1 | 9.3 | 9.0 |
| 6.00 | 12.5 | 10.6 | 9.7 |
| C14 | | | |
| 0.00 | n.d | n.d | n.d |
| 0.75 | 2.6 | 3.9 | 4.1 |
| 1.25 | 5.7 | 4.8 | 6.2 |
| 2.10 | 9.6 | 8.5 | 10.2 |
| 3.50 | 11.5 | 10.6 | 12.5 |
| 6.00 | 14.0 | 13.8 | 12.8 |
| C18 | | | |
| 0.00 | n.d | n.d | n.d |
| 0.75 | 3.6 | 5.2 | 5.9 |
| 1.25 | 7.5 | 8.9 | 9.2 |
| 2.10 | 8.3 | 9.7 | 12.8 |
| 3.50 | 14.3 | 12.0 | 15.7 |
| 6.00 | 16.2 | 12.9 | 15.7 |

TABLE 3

Uptake of alkylated porphyrins by flies as a function of the exposure time of porphyrin-containing bait to the flies.

| Exposure time | Recoveries (nmoles of porphyrin per fly) | | |
|---|---|---|---|
| (time) | C. capitata | B. oleae | S. calcitrans |
| C12 | | | |
| 3 h | 1.2 | 0.8 | 1.4 |
| 12 h | 3.9 | 2.6 | 3.2 |
| 24 h | 4.1 | 3.2 | 3.7 |
| C14 | | | |
| 3 h | 2.9 | 2.2 | 2.4 |
| 12 h | 5.3 | 3.7 | 5.6 |
| 24 h | 5.7 | 4.8 | 6.2 |
| C18 | | | |
| 3 h | 3.1 | 1.6 | 3.2 |
| 12 h | 6.6 | 7.7 | 8.9 |
| 24 h | 7.5 | 8.9 | 9.2 |

Porphyrin Concentration in the Bait: 1.24 µM

Table 4 shows the rate of alkylated porphyrin release from flies as a function of time after insect feeding with bait has been interrupted.

TABLE 4

Time dependence of alkylated porphyrin release by flies that had been exposed to 1.25 µM porphyrin in the bait.

| Exposure time | Recoveries (nmoles of porphyrin per fly) | | |
|---|---|---|---|
| (time) | C. capitata | B. oleae | S. calcitrans |
| C12 | | | |
| 12 h | 2.6 | 2.5 | 2.8 |
| 24 h | 1.1 | 1.4 | 2.0 |
| 48 h | 0.7 | 0.8 | 0.9 |

TABLE 4-continued

Time dependence of alkylated porphyrin release by flies that had been exposed to 1.25 µM porphyrin in the bait.

| Exposure time | Recoveries (nmoles of porphyrin per fly) | | |
|---|---|---|---|
| (time) | C. capitata | B. oleae | S. calcitrans |
| C14 | | | |
| 12 h | 3.0 | 3.2 | 4.3 |
| 24 h | 1.8 | 2.0 | 2.2 |
| 48 h | 0.7 | 0.6 | 0.8 |
| C18 | | | |
| 12 h | 3.7 | 3.8 | 4.2 |
| 24 h | 2.2 | 1.7 | 2.3 |
| 48 h | 1.0 | 0.6 | 1.1 |

Table 5 shows the effect of alkylated porphyrin concentration on the survival of *Ceratitis capitata* flies that had been fed for 24 h. For comparison, data obtained with two conventional porphyrins (as those described in WO 97/29637) offered to the insects for 24 h at a 3.0 and 8.1 µmolar concentration in the same bait are also shown. In all cases, the survival was determined 12 hours after changing food supply from a porphyrin-containing to a porphyrin-free bait.

TABLE 5

Effect of alkylated porphyrin concentration on the survival of *Ceratitis capitata* flies that had been fed with a porphyrin-containing bait for 24 h. The survival was measured 12 h after interruption of the feeding with the porphyrin-containing bait, which was replaced by a porphyrin-free bait.

| Porphyrin concentration | Survival (% of control untreated flies) | | | | |
|---|---|---|---|---|---|
| (µM) | C12 | C14 | C18 | Hp | C1 |
| 0.00 | 100 | 100 | 100 | 100 | 100 |
| 0.75 | 100 | 100 | 100 | — | — |
| 1.25 | 73 | 51 | 42 | — | — |
| 2.10 | 58 | 38 | 29 | — | — |
| 3.00 | 42 | 21 | 12 | 100 | 100 |
| 5.00 | 38 | 14 | 2 | — | — |
| 8.10 | 35 | 9 | 0 | 100 | 100 |

Hp = Haematoporphyrin
C1 = Meso-tetra (N-methyl-pyridyl) porphine.

Table 6 shows the same experiment described in Table 5, that was carried out with *Bactrocera oleae*.

TABLE 6

Effect of alkylated porphyrin concentration on the survival of *Bactrocera oleae* flies that had been fed with a porphyrin-containing bait for 24 h. The survival was measured 12 h after interruption of the feeding with the porphyrin-containing bait, which was replaced by a porphyrin-free bait.

| Porphyrin concentration (µM) | Survival (% of control untreated flies) | | |
|---|---|---|---|
| | C12 | C14 | C18 |
| 0.00 | 100 | 100 | 100 |
| 0.75 | 100 | 100 | 100 |
| 1.25 | 100 | 100 | 100 |
| 2.10 | 85 | 69 | 53 |
| 3.00 | 72 | 50 | 39 |
| 5.00 | 58 | 37 | 16 |
| 8.10 | 51 | 19 | 3 |

Table 7 shows the same experiment described in Table 5, that was carried out with *Stomoxis calcitrans*.

TABLE 7

Effect of alkylated porphyrin concentration on the survival of *Stomoxis calcitrans* flies that had been fed with a porphyrin-containing bait for 24 h. The survival was measured 12 h after interruption of the feeding with the porphyrin-containing bait, which was replaced by a porphyrin-free bait.

| Porphyrin concentration (μM) | Survival (% of control untreated flies) | | |
|---|---|---|---|
| | C12 | C14 | C18 |
| 0.00 | 100 | 100 | 100 |
| 0.75 | 100 | 100 | 100 |
| 1.25 | 82 | 77 | 79 |
| 2.10 | 64 | 52 | 45 |
| 3.00 | 47 | 31 | 24 |
| 5.00 | 29 | 11 | 10 |
| 8.10 | 16 | 3 | 0 |

Figure 2:
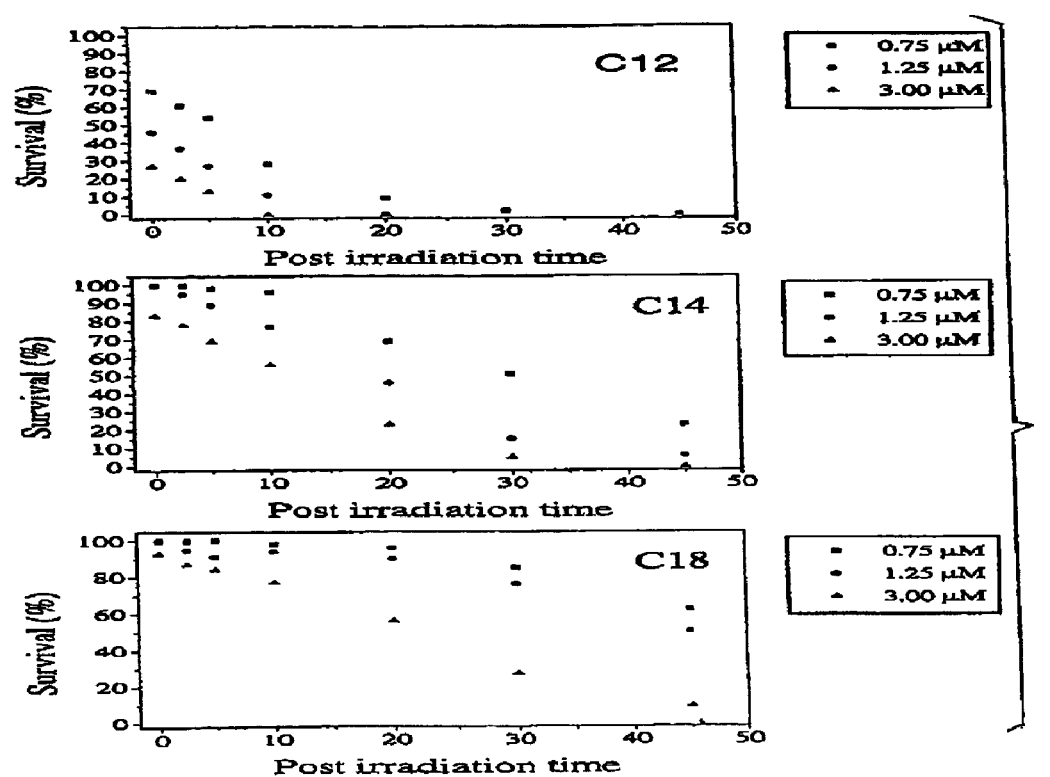
Figure 3:
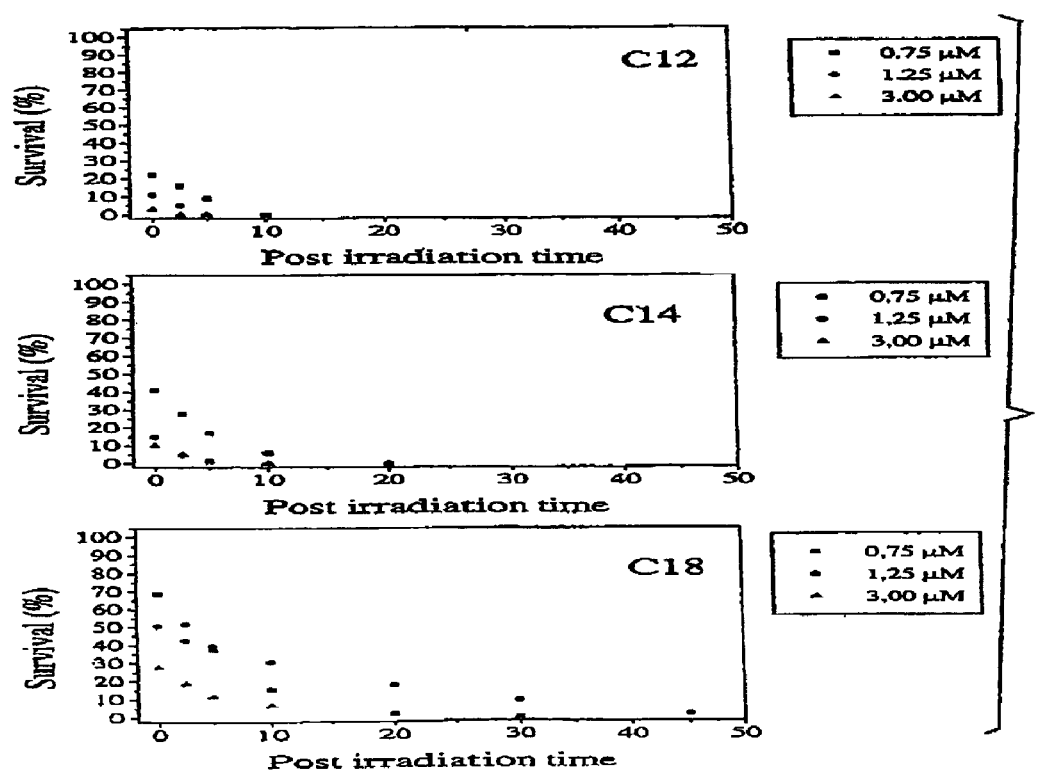

FIGS. 1, 2 and 3 show the effect of the alkylated porphyrin concentration in the bait on the survival of visible light-irradiated (1220 $\mu E\ s^{-1}m^{-2}$) *C. capitata*, and *B. oleae* and *S. calcitrans* flies, respectively, that had been fed for 24 h with a porphyrin-containing bait. The irradiations were performed for 1 h, then the flies were kept in dim light for monitoring the survival. Control flies were irradiated under identical conditions after feeding with a porphyrin-free bait.

Table 8 shows the effect of the time interval between feeding the flies for 24 h with a bait containing 3 μM alkylated porphyrin and irradiation on the survival of *Ceratitis capitata* flies. The irradiations were performed for 1 h at a fluence-rate of 1220 $\mu E\ s^{-1}m^{-2}$. The survival was evaluated 10 h after the end of irradiation. For comparison purposes, the data obtained in parallel experiments using two traditional previously studied porphyrins (as disclosed in WO 97/29637) are also shown. The porphyrins are abbreviated as following: HP: haematoporphyrin; C1: meso-tetra(N-methyl-pyridyl)porphine.

TABLE 8

Effect of the time interval between administration of a porphyrin-containing bait and irradiation on the survival of *Ceratitis capitata*.

| Time interval (h) | Survival (% of control untreated flies) | | | | |
|---|---|---|---|---|---|
| | C12[a] | C14[a] | C18[a] | Hp[b] | C1[b] |
| 0 | 4 | 0 | 45 | 20 | 90 |
| 12 | 8 | 0 | 52 | 37 | 94 |
| 24 | 23 | 10 | 64 | 58 | 100 |
| 48 | 37 | 21 | 70 | 61 | 97 |

[a]Alkylated porphyrins, 3 μM
[b]Traditional porphyrins, 8 μM

Table 9 shows the effect of the irradiation fluence-rate on the photoinduced decrease in survival of *Ceratitis capitata* flies that were irradiated 12 h after feeding for 24 h with a bait containing 3 μM alkylated porphyrins. The survival was evaluated 10 h after the end of irradiation.

TABLE 9

Effect of irradiation fluence-rate on survival of *Ceratitis capitata* flies that were irradiated 24 h after feeding with a porphyrin-containing bait.

| Fluence-rate ($\mu E\ s^{-1}m^{-2}$) | Survival (% of control untreated flies) | | | | |
|---|---|---|---|---|---|
| | C12[a] | C14[a] | C18[a] | Hp[b] | C1[b] |
| 760 | 13 | 10 | 52 | 81 | 100 |
| 1220 | 4 | 0 | 45 | 20 | 90 |
| 1500 | 2 | 0 | 40 | 11 | 81 |
| 2000 | 0 | 0 | 31 | 8 | 73 |

[a]Alkylated porphyrins, 3 μM
[b]Traditional porphyrins, 8 μM

Table 10 shows the effect of irradiation time on the survival of *Ceratitis capitata* flies that have been irradiated with sunlight (average intensity 1150 $\mu E\ s^{-1}m^{-2}$) 12 h after feeding for 24 h with a bait containing 3 μM alkylated porphyrins. The survival was evaluated 1 h after the end of irradiation.

TABLE 10

Effect of irradiation time on the survival of *Ceratitis capitata* flies that were exposed to sunlight at 12 h after feeding with a porphyrin-containing bait.

| Irradiation time (min.) | Survival (% of control untreated flies) | | | | |
|---|---|---|---|---|---|
| | C12[a] | C14[a] | C18[a] | Hp[b] | C1[b] |
| 15 | 33 | 21 | 80 | 75 | 100 |
| 30 | 17 | 10 | 75 | 70 | 100 |
| 45 | 10 | 0 | 61 | 64 | 93 |
| 60 | 2 | 0 | 31 | 40 | 97 |

[a]Alkylated porphyrins, 3 μM
[b]Traditional porphyrins, 8 μM

1. Starvation and Feeding Phases (Table 1)

An appropriate number of flies (50 flies per each experiment) was caged in 115×55×70 mm Plexiglas cages with several holes (ø=0.5 mm) and starved for 36 h. Then, depending on the protocol to be adopted for each specific experiment, the flies were fed with the bait (10% sucrose and 1% autolysed yeast in neutral aqueous solution), which was either porphyrin-free or added with a predetermined concentration of the porphyrin. These flies were then used in the various experimental sessions.

2. Studies of Porphyrin Uptake and Release by the Flies (Tables 2, 3 and 4)

At predetermined times, the flies were sacrificed by freezing; the dead flies were then homogenized with a Polytron in 10 ml of a 2% aqueous solution of sodium dodecylsulphate (SDS). The suspension was centrifuged for 10 min at 2,000 rpm, the pellet was discarded and known aliquots of the supernatant were diluted by means of a chloroform/methanol binary mixture (1/2, v/v). The porphyrin concentration was measured by reading the fluorescence emitted at wavelengths above 630 nm and interpolating the emission intensity with a calibration plot obtained with known amounts of the porphyrin. The results were expressed as nanomoles of porphyrin recovered per fly.

It is apparent that the amount of porphyrin accumulated by the flies increased with both the porphyrin concentration in the bait and the exposure time of the bait to the insects. No saturation effect was observed even at the highest porphyrin concentration. The efficiency of porphyrin uptake also increased with an elongation of the alkyl chain from 12 to 18 carbon atoms, in agreement with the well known tendency of hydrophobic porphyrins to display a larger affinity for many cell types. Moreover, clearly detectable porphyrin concentrations were recovered from all the types of flies studied by us 48 h after interruption of the porphyrin supply; this could suggest that the toxic effect of the porphyrin on the flies is persistent for prolonged periods of time.

3. Insecticidal Action of Alkylated Porphyrins in the Dark (Tables 5, 6 and 7)

The response of the flies to the treatment with alkylated porphyrins in the absence of light was determined upon feeding with increasing porphyrin concentrations (up to 8.1 µM in the bait. The number of survivors was evaluated 12 h after switching from administration of a porphyrin-containing bait to a porphyrin-free bait. In none of the experiments was mortality or any apparent toxic effect observed in control flies (flies not fed with porphyrin, see survival at 0 µM porphyrin concentration).

Quite surprisingly and unexpectedly, all three alkylated porphyrins caused a readily detectable insect death at doses as low as 1.25-2.10 µM and the phenomenon was clearly enhanced at larger porphyrin doses. The toxic effect was particularly apparent in the case of *C. capitata* and *S. calcitrans*, althogh also *B. oleae* exhibited a significant susceptibility. This behaviour is not typical of porphyrins, which are known to act as photosensitizing agents, namely to induce an appreciable cytotoxicity only when activated by irradiation with visible light (see, for example, Jori G. and Spikes J. D., Photobiochemistry of porphyrins, in *Topics in Photomedicine*, Smith K. C., ed., Plenum Press, New York, 1983, pp. 183-319). As a matter of fact, as shown in Table 5, when two traditional porphyrins of the type described in patent application WO97/29637 (such as HP and C1) were administered to *C. capitata*, no mortality of the flies was observed even at the largest porphyrin dose.

It is likely that the long hydrocarbon chain which is attached in the periphery of the tetrapyrrolic macrocycle acts as an arm interfering with the native three-dimensional organization of the membranous cell domains thereby impairing some critical cellular functions. This hypothesis is supported by the observation that the extent of the porphyrin-induced lethal effect increases from C12 to C14 and C18, namely with increasing length of the alkyl chain.

In any case, this unexpected "dark" toxic activity of the alkylated porphyrins marks a neat advantage as compared with other porphyrin compounds since it extends the insecticidal effect beyond the sunshine hours, prolonging the action for 24 h a day. As one can deduce from Table 4, about 20-25% of the porphyrin present 12 h after porphyrin supply was still present in the flies after 48 h. Thus, it appears reasonable to hypothesize that the toxic action of alkylated porphyrins persists for at least two days.

4. Insecticidal Action of Alkylated Porphyrins upon Irradiation with Visible Light (or Sunlight) (see Tables 8, 9 and 10 and FIGS. 1, 2 and 3).

FIG. 1 shows the effect of the alkylated porphyrin concentration in the bait of the survival of visible light-irradiated (1,220 µE s$^{-1}$m$^{-2}$) *C. capitata* flies that were fed for 24 hours with a porphyrin-containing bait. The irradiations were performed for 1 h, then the flies were kept in a dim light for observing the survival rate. Control flies were irradiated under identical conditions after feeding them with a porphyrin-free bait.

FIG. 2 illustrates the effect of the alkylated porphyrin concentration in the bait of the survival of visible light-irradiated (1,220 µE s$^{-1}$m$^{-2}$) *B. oleae* flies that were fed for 24 h with porphyrin-containing bait. The irradiations were performed for 1 h, then the flied were kept in dim light for observing the survival rate. Control flies were irradiated under identical conditions after feeding with a porphyrin-free bait.

FIG. 3 shows the effect of the alkylated porphyrin concentration in the bait of the survival of visible light-irradiated (1,220 µE s$^{-1}$m$^{-2}$) *S. calcitrans* flies that were fed for 24 h with a porphyrin-containing bait. The irradiations were performed for 1 h, then the flies were kept in dim light for observing the survival rate. Control flies were irradiated under identical conditions after feeding with a porphyrin-free bait.

As expected, all three alkylated porphyrins retained the photosensitizing activity which is typical of this class of compounds, hence their insecticidal activity as expressed after administration in the dark was further enhanced when the porphyrin-fed flies were exposed to full spectrum visible light from an artificial light source or to natural sunlight. Thus, a 0.75 µM alkylated porphyrin dose, which was essentially ineffective in the dark, caused a readily detectable fly mortality upon irradiation. Once again, the phototoxic effect became more pronounced in the presence of larger porphyrin doses. The most efficient insecticidal action was caused by C14, whereas a drop in the overall photoactivity was observed for the C18 porphyrin in spite of its greater uptake by the flies. This apparently contradictory behaviour could be related to the known tendency of most hydrophobic porphyrins to undergo an aggregation process in polar media, which markedly decreases their photosensitizing efficiency (see Jori G. and Spikes J. D., referred to above). In any case, in the presence of the C14 derivative, essentially all flies died within about 45 min. after 1 h illumination with artificial light or sunlight. The photoinsecticidal action remained at a high level up to at least 48 h after feeding the flies with the alkylated porphyrins and was modulated by the light intensity (fluence-rate). Very high mortality levels were achieved by using a fluence-rate around 1200 µE s$^{-1}$m$^{-2}$ which corresponds to a typical sunlight intensity in mid-June or mid-September at a Northen Italy latitude. However, the photoactivity was still noticeable at lower fluence-rates, e. g. 760 µE s$^{-1}$m$^{-2}$.

Quite interestingly, the photoinsecticidal activity of C12 and C14 was by far greater than that exhibited by classical porphyrins, such as HP and C1: the two former porphyrins caused a markedly larger drop in the survival of flies even when administered at a 3 µM dose versus a 8 µM dose of traditional porphyrins. The appreciably increased phototoxicity of alkylated porphyrins was confirmed under all the experimental conditions tested by us, particularly when sunlight was used for activating the porphyrins.

Since a variety of porphyrin analogs, i. e. compounds sharing the presence of a tetrapyrrolic macrocycle with porphyrins (e. g. chlorins, phthalocyanines, naphthalocyanines), have been repeatedly shown to possess equivalent photosensitizing properties both in vitro and in vivo (see, for example, van Lier J. E. and Spikes J. D. in *Photosensitizing Compounds: their Chemistry, Biology and Clinical Use*, Wiley Publishing Co., Chichester, 1989, pp. 17-32; Jori G., Photosensitizers: approaches to enhance the selectivity and efficiency of photodynamic action, *J. Photochem. Photobiol., B:Biol.* 36:87-93, 1996; Spikes J. D., Photobiology of porphyrins, in: *Porphyrin Localization and Treatment of Tumors*, Alan R. Liss, New York, 1994, pp. 19-39), it appears reasonable to assume that a similar pattern of peripheral substitution will endow the above mentioned porphyrinoids with a highly efficient insecticidal activity in the dark, as well as in the presence of visible light.

In actual fact, the phthalocyanine structure can be modulated at different levels, namely by inserting different metal ions M at the centre of the macrocycle, by changing the type and number (1 to 8) of the peripheral substituents R, and by introducing axial ligands $L_1$, and $L_2$ to the central metal ion. Such chemical features are illustrated in the following molecular structure:

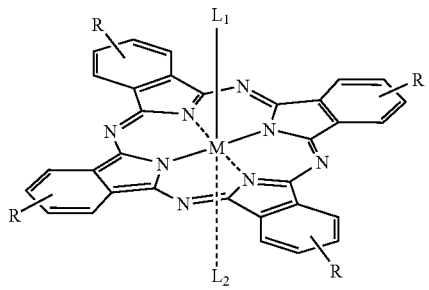

M = metal ion
R = peripheral substituent
L = axial ligand

We have surprisingly found that the impartment of amphiphilic properties through the choice of suitable polar axial ligands is also endowing the phthalocyanine with an efficient insecticidal activity. Thus, the use of $L_1$, and $L_2$=—O—Si—[O—$CH_2$—$CH_2$—$CH_2$—$CH_2$—$N(CH_3)^+]_3$ generated a phthalocyanine derivative which caused a 82% decrease in survival of Ceratitis capitata and 50% decrease in survival of Bactrocera oleae upon exposure for 1 h to full spectrum visible light (1220 µE $s^{-1}$ $m^{-2}$) after exposure of the flies to a bait containing 3 mM phthalocyanine for 24 h. In both cases the survival was determined at 12 h after the end of illumination. Therefore, the phthalocyanine of the above mentioned structure appears to be at least as active as porphyrins C12 and C14 against the two classes of flies studied by us. This can be deduced by a comparison of the present data with those reported in Tables 5 and 6.

The above described invention is susceptible to numerous modifications and changes within the scope as defined by the claims.

What is claimed is:

1. An insecticidal composition comprising:
   at least one phthalocyanine compound of general chemical structure

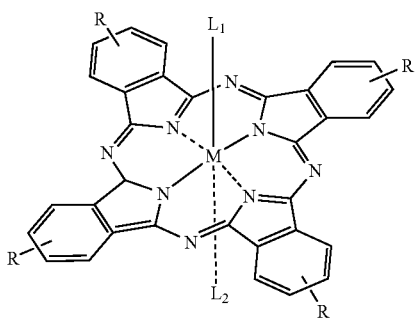

wherein
M represents a hexacoordinated metal,
R is a peripheral substituent in any number between 1 and 8 and is a saturated hydrocarbon chain containing 1 to 20 carbon atoms, and
$L_1$ and $L_2$ are axial ligands of cationic nature as given by the presence of quaternary ammonium salts.

2. The insecticidal composition as claimed claim 1, an attractant agent for insects or pests.

3. The insecticidal composition as claimed in claim 2, wherein said attractant agent is of biological nature.

4. The insecticidal composition as claimed in claim 2, wherein said attractant agent is a chemical agent.

5. The insecticidal composition as claimed in claim 2, wherein said attractant agent is a pheromone.

6. The insecticidal composition as claimed in claim 5, wherein said pheromone is selected from the group consisting of Bompycol, Brevicomin, Disparlur, Frontalin and Grandisol.

7. The insecticidal composition as claimed claim 1, wherein in said at least one phthalocyanine compound, $L_1$ and $L_2$ are —O—Si[O—$CH_2$—$CH_2$—$CH_2$—$CH_2$—$N(CH_3)^+]_3$.

8. A method of enhancing the pesticidal activity of an insecticidal or pesticidal composition, said composition comprising at least one phthalocyanine compound of general chemical structure

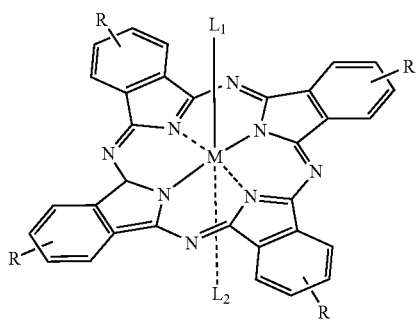

wherein
M represents a hexacoordinated metal,
R is a peripheral substituent in any number between 1 and 8 and is a saturated hydrocarbon chain containing 1 to 20 carbon atoms, and
$L_1$ and $L_2$ are axial ligands of cationic nature as given by the presence of quaternary ammonium salts, wherein said method comprises:
irradiating the composition with an artificial light source which is at least one selected from the group consisting of a high pressure Xenon lamp, a fluorescent lamp and a tungsten lamp.

9. The method as claimed in claim 8, wherein said light source is operated at a fluence-rate between 500 and 2,000 µE $s^{-1}m^{-2}$.

10. The method as claimed in claim 9, wherein the fluence-rate ranges between 1,000 and 1,500 µE $s^{-1}m^{-2}$.

* * * * *